United States Patent [19]
Koshino

[11] Patent Number: 5,137,536
[45] Date of Patent: Aug. 11, 1992

[54] TIBIAL COMPONENT FOR ARTIFICIAL KNEE JOINT

[75] Inventor: Tomihisa Koshino, Yokohama, Japan

[73] Assignee: Nariko Koshino, Yokohama, Japan

[21] Appl. No.: 655,989

[22] Filed: Feb. 15, 1991

[30] Foreign Application Priority Data

Mar. 16, 1990 [JP] Japan .................................. 2-65939

[51] Int. Cl.⁵ .................................................. A61F 2/38
[52] U.S. Cl. ............................................. 623/20; 623/18
[58] Field of Search ........................................... 623/18

[56] References Cited

U.S. PATENT DOCUMENTS

| | | | |
|---|---|---|---|
| 4,205,400 | 6/1980 | Shen et al. ............... | 623/20 X |
| 4,501,031 | 2/1985 | McDaniel et al. .......... | 623/20 |
| 4,759,767 | 7/1988 | Lacey ....................... | 623/20 |
| 4,822,362 | 4/1989 | Walker et al. ............. | 623/20 |
| 4,883,488 | 11/1989 | Bloebaum et al. ......... | 623/20 |
| 4,938,769 | 7/1990 | Shaw ........................ | 623/20 |
| 4,944,756 | 7/1990 | Kenna ....................... | 623/20 |
| 4,944,757 | 7/1990 | Martinez et al. .......... | 623/20 |

Primary Examiner—Randall L. Green
Assistant Examiner—D. Willse
Attorney, Agent, or Firm—Nixon & Vanderhye

[57] ABSTRACT

In a tibial component for use with a femoral component for an artificial knee joint, a plate section has, at its upper face, a pair of bearing surface parts which are in sliding contact with the femoral component. A stem extends downwardly from a lower face of the plate section. A pair of blade-like plicae extend obliquely posteriorly from the stem and extend from the lower face of the plate section downwardly.

36 Claims, 6 Drawing Sheets

TIBIAL COMPONENT FOR ARTIFICIAL KNEE JOINT

BACKGROUND OF THE INVENTION

The present invention relates to a tibial component for an artificial knee joint.

An artificial knee joint coping with symptoms of a knee comprises a femoral component and a tibial component. In the case where the knee is replaced with the artificial knee joint, joint portions including a distal part of the femur and a proximal part of the tibia, which are to be replaced, are resected, and the femoral component and the tibial component are fixedly inserted respectively into the distal part of the femur and the proximal part of the tibia.

The tibial component of this kind referred to above is known from, for example, Japanese Patent Provisional Publication No. SHO 64-68256. In this case, a stem extends straight downwardly substantially from a center of a lower face of a plate section. Further, a pair of laterally directed triangular fins extend from the lower face of the plate section, at both medial and lateral sides of the stem, and a pair of antero-posteriorly directed fins extend downwardly from the lower face of the plate section at the lateral ends of the respective laterally directed fins. Accordingly, the laterally directed fins and the antero-posteriorly directed fins are formed into a double T-shaped configuration.

The laterally directed fins and the antero-posteriorly directed fins prevent the tibial component from rotation about the longitudinal axis of the tibia. Further, the laterally directed fins support a load in the antero-posterior direction, while the antero-posteriorly directed fins support a load in the lateral direction. Accordingly, the tibial component has such a function as to prevent inclination in the antero-posterior and medio-lateral directions.

However, the above-described tibial component has the following disadvantages. That is, since the tibial component is provided with the two laterally directed and two antero-posteriorly directed fins, the bone is fractioned so that an interruption in blood circulation occurs in the bone. Further, there are many projections or corners of the bone formed by the fins, and the projections or the corners causes the bone necrosis. Moreover, in a case with deep wear in the tibial plateau, the upper end of the tibia has to be osteotomized largely in a horizontal plane, so that the lower downwardly from the upper end of the tibia the level of osteotomy, the more reduced the inner diameter of the tibia. Accordingly, in the component in which, as described above, the laterally directed fins of the tibial component are projected out far away from the central axis of the component, these laterally directed fins may destroy the cortex of the tibia at implantation, and the stability of an implanted component is reduced. Furthermore, since there are many numbers of fins, molding or forming is difficult. Further, since the total cross-sectional area of the fins is larger, driving into the tibia is more difficult.

SUMMARY OF THE INVENTION

It is therefore an object of this invention to provide a tibial component of an artificial knee joint, which can prevent rotation and inclination in antero-posterior and media-lateral directions, in which an interruption in blood circulation, the bone necrosis and destruction of the tibia are very rarely to occur, and which is easy to be manufactured and to be driven into the bone.

According to the invention, there is provided a tibial component for use with a femoral component for an artificial knee joint, the tibial component comprising:
- a plate section having, at its upper face, a pair of bearing surface parts which are in sliding contact with the femoral component;
- a stem extending downwardly from a lower face of the plate section; and
- a pair of blade-like plicae extending obliquely posteriorly from the stem and extending from a lower face of the plate section downwardly.

In this case, it is desirable that the pair of blade-like plicae defines therebetween an angle of 80° to 140°.

Further, it is desirable that the stem is formed at a location adjacent a front part of the plate section from a center thereof, and is inclined posteriorly with respect to a perpendicular to the lower face of the plate section. In this case, it is desirable that the stem is inclined through 2° to 10° posteriorly with respect to the perpendicular to the lower face of the plate section. Furthermore, it is desirable that the stem has its length which is 20% to 75% of a dimension of the plate section in a medial and lateral direction and which is 40% to 90% of a dimension of the plate section in an antero-posterior direction. It is still preferable that the stem is rectangular in cross-section.

Moreover, it is desirable that, at a location between the pair of blade-like plicae, the plate section is formed with a curved cut-out into which a posterior cruciate ligament is to be inserted.

Further, when the pair of bearing surface parts are considered as a single bearing surface portion, the single bearing surface portion is curved such that an anterior side of the single bearing surface portion is higher in elevation than a posterior side of the single bearing surface portion, and a central side of the single bearing surface portion is higher in elevation than medial and lateral sides of the single bearing surface portion.

Furthermore, it is desirable that the tibial component further comprises a projection formed within a central region of the upper face of the plate section.

With the arrangement of the tibial component according to the invention, since the pair of blade-like plicae extend from the stem obliquely and posteriorly, there are provided not only such a function as to prevent rotation of the tibial component, but also such a function as to prevent inclination in the antero-posterior and medio-lateral directions of the tibial component. Further, the blade-like plicae have such advantages that an interruption in blood circulation, the bone necrosis and destruction are very rarely to occur, and driving and manufacturing of the tibial component are made easy.

DESCRIPTION OF THE EMBODIMENTS

Figure 1:
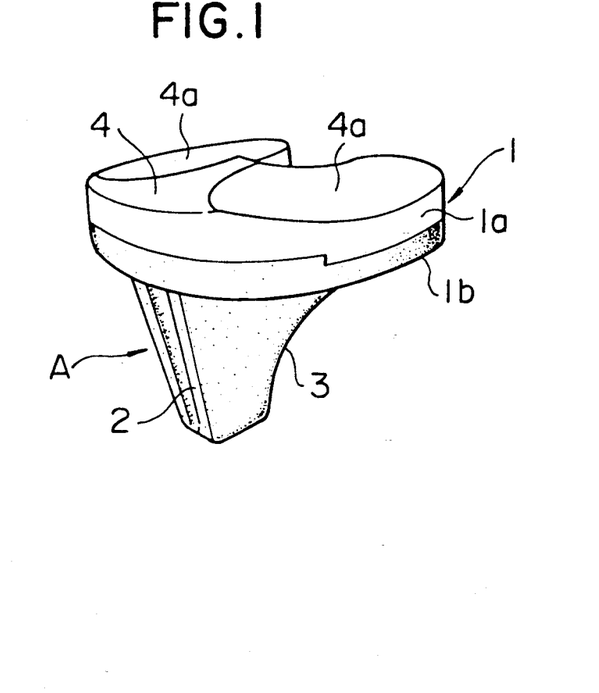
FIG. 1 is a perspective view of a tibial component of an artificial knee joint, according to a first embodiment of the invention, as viewed from the obliquely upward side.
Figure 2:
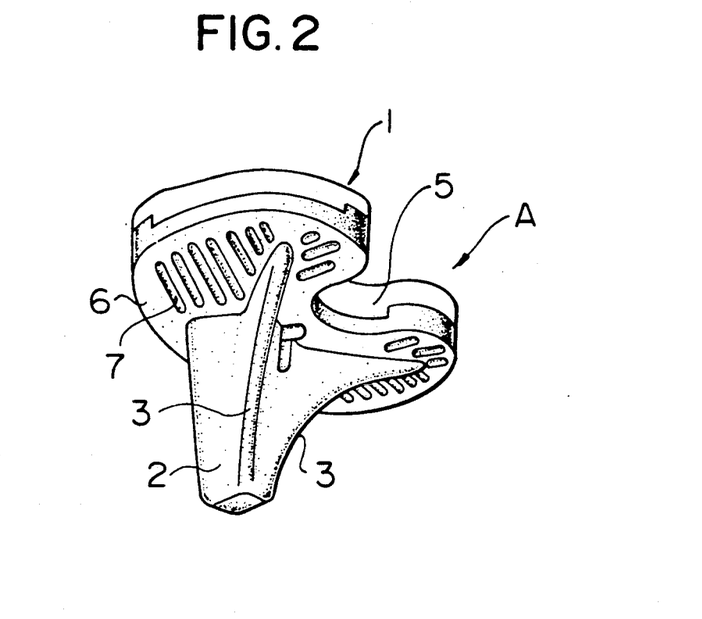
FIG. 2 is a perspective view of the tibial component illustrated in FIG. 1, as viewed from the obliquely downward side.
Figure 3:
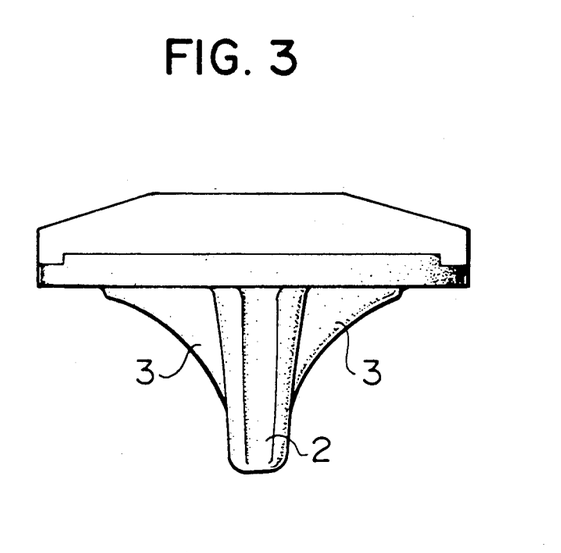
FIG. 3 is a front elevational view of the tibial component illustrated in FIGS. 1 and 2.
Figure 4:
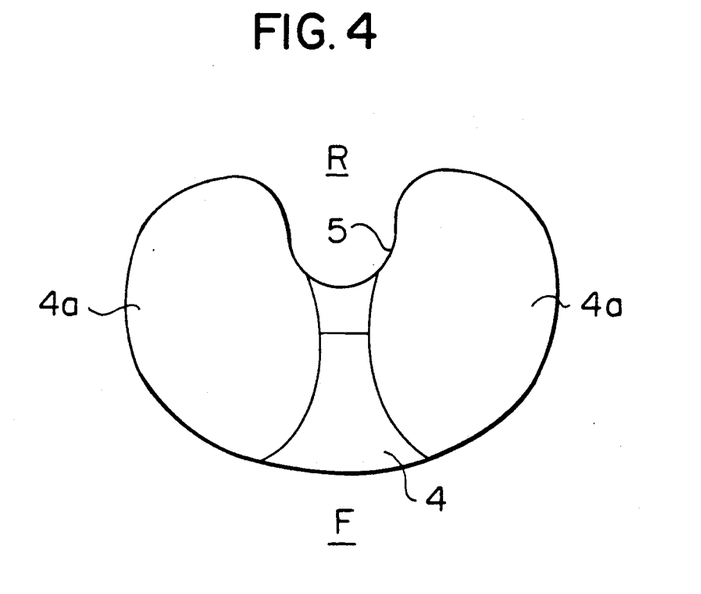
FIG. 4 is a top plan view of the tibial component illustrated in FIGS. 1 and 2.
Figure 5:
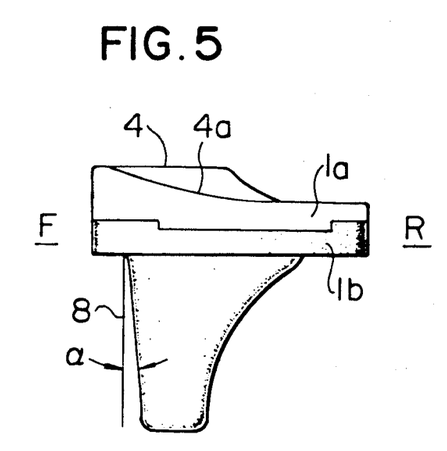
FIG. 5 is a right-hand side elevational view of the tibial component illustrated in FIGS. 1 and 2.
Figure 6:
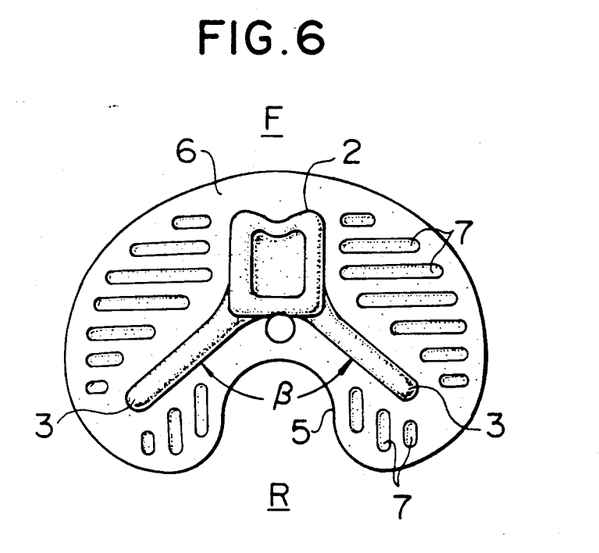
FIG. 6 is a bottom view of the tibial component illustrated in FIGS. 1 and 2.
Figure 7:
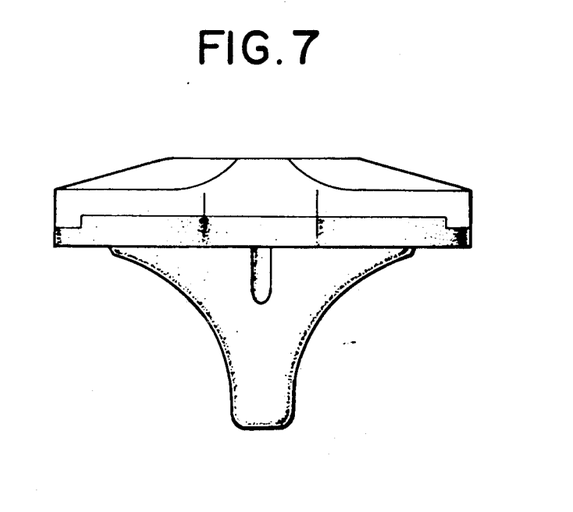
FIG. 7 is a posterior view of the tibial component illustrated in FIGS. 1 and 2.

Referring first to FIGS. 1 through 7, there is shown a tibial component A according to a first embodiment of the invention. In FIG. 1, the tibial component A is seen obliquely from the above, while, in FIG. 2, the tibial component A is seen obliquely from the below. FIG. 3 is a front elevational view of the tibial component A. FIG. 4 is a top plan view of the tibial component A. FIG. 5 is a right-hand side elevational view of the tibial component A. FIG. 6 is a bottom view of the tibial component A. FIG. 7 is a posterior view of the tibial component A. In this connection, in the following description, the anterior side and the posterior side mean a direction under the condition that the tibial component A is inserted into the tibia. The anterior side is indicated by the reference character F in FIGS. 5 and 6, while the posterior side is indicated by the reference character R.

The tibial component A substantially comprises a plate section 1 receiving a load from the femoral side and a stem 2 to be inserted into an upper portion of the tibia, and a pair of blade-like plicae 3 and 3 to be inserted into the upper portion of the tibia.

The plate section 1 is composed of a receiving portion 1a and a pedestal portion 1b which are fixedly connected to each other by, for example, dovetail fitting. The receiving portion 1a is made of a wear-resistant material such as, for example, HDPE (high density polyethylene). The receiving portion 1a has its upper face 4 whose pair of bearing surface parts 4a and 4a are in sliding contact with a femoral component. As shown in FIGS. 5 and 7, the pair of bearing surface parts 4a and 4a are curved such that the anterior side of each bearing surface part is higher in elevation than the posterior side of the bearing surface part, and the central sides of the respective bearing surface parts are higher in elevation than the medial and lateral sides of the respective bearing surface parts. The pedestal portion 1b is formed in integral relation to the respective upper ends of the stem 2 and the blade-like plicae 3 and 3. The pedestal portion 1b is made of ceramics such as, for example, polycrystal of alumina or the like.

The plate section 1 is formed, at its posterior side, with a curved cut-out 5 into which a posterior cruciate ligament and its surrounding bone are to be inserted. Accordingly, the tibial component A is a component of the posterior cruciate ligament pressing type, which does not sacrifice the posterior cruciate ligament. The cut-out 5 has its interior which is in the form of a semi-circle whose diameter is approximately from about 15 mm to 25 mm, for example.

The plate section 1 has its lower face 6 which is formed therein with a plurality of shallow grooves 7 for improving affinity with respect to the bone. The aforesaid stem 2 extends downwardly from the lower face 6. In this case, the stem 2 extends downwardly from a portion of the lower face 6, which is located adjacent the anterior side F with respect to the center of the lower face 6. As shown in FIG. 5, the stem 2 is inclined toward the posterior side R with respect to a perpendicular 8 to the lower face 6 through an angle $\alpha$ of, for example, 2° to 10°, preferably, through an angle of 4° to 6°. The stem 2 has its cross-sectional configuration which is substantially rectangular. As shown in FIG. 6, the cross-sectional area of the stem 2 is reduced gradually toward the lower end of the stem 2, that is, away from the plate section 1.

The pair of blade-like plicae 3 and 3 are so formed as to extend obliquely posteriorly from the stem 2. The blade-like plicae 3 and 3 have their respective upper ends which are contiguous to the lower face 6 of the plate section 1. As shown in FIGS. 3 and 7, the edges of the respective blade-like plicae 3 and 3 on the lower side are curved. As shown in FIG. 6, the pair of blade-like plicae 3 and 3 defines therebetween an angle $\beta$ of, for example, 80° to 140°, preferably, of about 95° to 105°. The aforementioned cut-out 5 is located between the pair of blade-like plicae 3 and 3.

In the case of the standard-type component for women or children, the dimensions or sizes of various parts are as follows. That is, for example, the stem 2 has its length of about 28 mm, the plate section 1 has its width in the medio-lateral or transverse direction, which is about 65 mm, and the plate section 1 has its length in an antero-posterior or longitudinal direction, which is about 44 mm. In the case of the large-type component for adult men, the length of the stem 2 is about 31 mm, the width of the plate section 1 in the medio-lateral direction is about 71 mm, and the length of the plate section 1 in the antero-posterior direction is about 48 mm.

The tibial component A of the construction described above is easy in forming or molding, because the tibial component A is simple in structure or construction.

Figure 8:
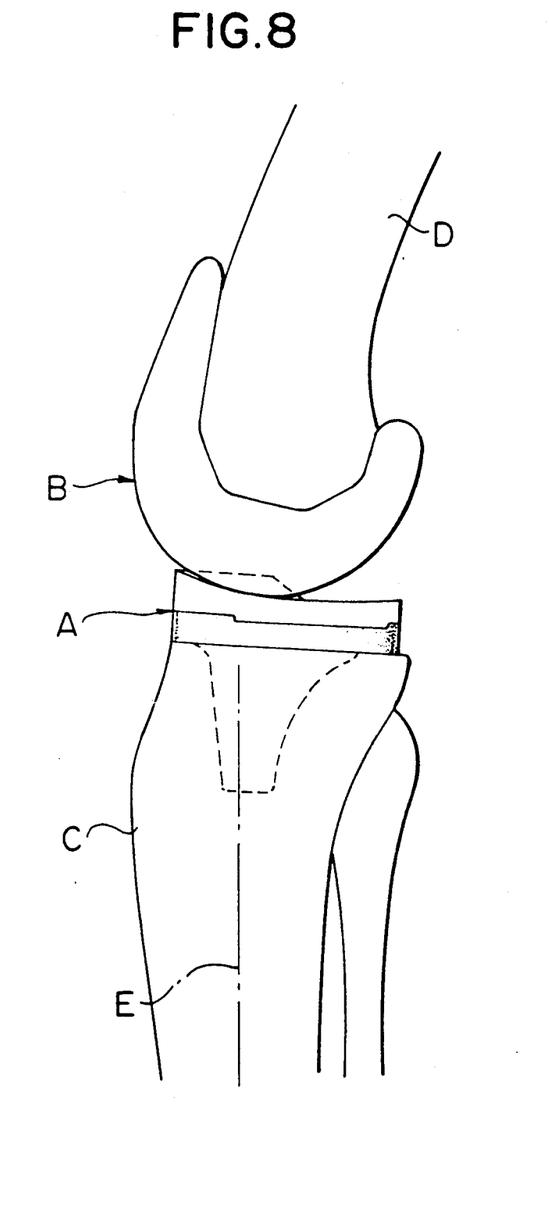
FIG. 8 is a view showing a condition in which the tibial component illustrated in FIGS. 1 and 2 and a femoral component are mounted to a knee joint.

FIG. 8 shows the lateral view of the knee joint to which the tibial component A and a femoral component B are implanted. It is possible to employ the femoral component B other than the possible to employ the femoral component B other than the illustrated one.

To implant the tibial component A into the tibia C, the proximal end of the tibia C is first osteotomized horizontally. A metallic instrument or a central stem impactor (punch) with its shape substantially being the same as the stem 2 and the blade-like plicae 3 and 3, is then driven into a bone marrow to form a hole. Thus, the bone marrow around the hole is compressed and hardened. For a patient with the porous bone especially for a case of rheumatoid arthritis or osteoporosis, the bone marrow is impacted in this manner, whereby the density of bones surrounding the tibial component A is increased. Accordingly, this is important since the tibial component A can be prevented from sinking and loosening. Subsequently, the tibial component A is driven into the hole of the bone marrow, and is implanted. By this procedure, the lower face 6 of the plate section 1 in the tibial component A is supported on or by the upper osteotomized surface of the tibia, and the stem 2 and the pair of blade-like plicae 3 and 3 are inserted into the bone marrow of the tibia C.

The stem of the tibial component A inserted into the tibia C is relatively small in volume and the blade-like plicae 3 and 3 do not fractionate the bone. Accordingly, an interruption in blood circulation and the corner bone necrosis of the tibia C are not brought about. Further, the main part of the blade-like plicae 3 and 3 are arranged around the step and are not separated from the axis of the tibia C, dissimilarly to the conventional one. Thus, the blade-like plicae 3 and 3 never destruct the cortex of the tibia even in a case with narrow diameter of the bone.

A load from the side of the femur D is received by the receiving portion 1a of the plate section 1. The load is supported by the upper face or osteotomized face of the tibia C through the lower face 6 of the plate section 1. Further, since the load is supported by the bone marrow through the blade-like plicae 3 and 3 and the stem 2, sinking of the tibial component A is small.

Furthermore, since the blade-like plicae 3 and 3 extend obliquely posteriorly from the stem 2 with the angle β defined between the blade-like plicae 3 and 3 as described previously, the tibial component A is prevented from rotation around the long axis E of the tibia C when the rotational force and the shearing force are applied to the tibial component A at joint motion, and the tibial component A is prevented from being inclined in the antero-posterior and medio-lateral directions.

Moreover, in consideration of the fact that, generally, the proximal part of the tibia C (tibial neck) is slightly inclined posteriorly with respect to the vertical line and, accordingly, the osteotomized surface of the tibia C is similarly inclined posteriorly with respect to the horizon, the tibial component A according to the first embodiment of the invention is constructed as follows. That is, as indicated by E in FIG. 8, the stem 2 is slightly inclined posteriorly by the angle α with respect to the perpendicular line 8 in such a manner that the long axis of the stem 2 is substantially in agreement with the long axis of the tibia C when the component A is driven into the tibia C. If the stem 2 is not inclined posteriorly, the stem 2 will project out anteriorly so that the long axis of the stem 2 becomes in disagreement with the long axis of the tibia C. Thus, bone destruction will be caused or induced dynamically in the tibia.

The blade-like plicae 3 and 3 of the tibial component A driven in the manner described above have such a function as to prevent sinking or subsidence of the tibial component A. Further, since the stem 2 is rectangular in cross-section, the stem 2 itself has such a function as to prevent rotation of the tibial component A.

As described above, the tibial component A sufficiently receives the force acting upon the joint, so that inclination in the antero-posterior and medio-lateral directions and rotation around the long axis can be prevented. Thus, there is no gap occurring between the tibial component A and the tibia C, and loosening between them is very rarely to occur. The loosening of the tibial component A is extremely disadvantageous because of various complications in the operated joint.

It is very important to make the gap difficult to make especially, in the cases with no use of bone cement such as one made of ceramics or the like.

Further, since the cut-out 5 substantially in the form of a semi-circle, whose diameter is about 15 mm to 25 mm, is formed in the posterior part of the plate section 1, it is possible to secure the sufficiently big bone at the insertion of the posterior cruciate ligament on the posterior side. Accordingly, it is possible to prevent occurrence of the complications which serve as an interruption in blood circulation of the insertion of the posterior cruciate ligament. Since it is unnecessary to cut the posterior cruciate ligament by the cut-out 5, original stability of the knee can be preserved or retained. Furthermore, the existence of the big anchoring bone around the insertion of the posterior cruciate ligament into the cut-out 5 redoubles fixing force of the tibial component to the tibia C, thereby preventing loosening. Moreover, since the cut-out 5 is circular in configuration, slight difference in rotational position of the tibial component found during surgery can be corrected or readjusted, and this is extremely advantageous in view of the surgical procedures.

The length of the stem 2 is about 20% to 75% of the transverse dimension or size of the plate section 1, preferably, 35% to 50% thereof, and 40% to 90% of the antero-posterior dimension of the plate section 1, preferably 50% to 70% thereof. If the length of the stem 2 is shorter than that described above, a fixing force is considerably made inferior. If the length of the stem 2 is longer than that described above, loosening at the distal end of the stem will increase. For example, if the length of the stem 2 is made twice, the amplitude of the loosening at the distal end is doubled. Thus, complications such as periosteum reaction, stress fracture of the bone or the like will be caused at the circumference of the distal end of the stem.

Furthermore, the pair of curved bearing surfaces 4a and 4a of the tibial component A prevent the femoral component B from being moved anteriorly, because the pair of curved bearing surfaces 4a and 4a are made to be high or thick in elevation toward the anterior side F. Moreover, since the central sides of the respective curved bearing surfaces 4a and 4a are made to be higher in elevation than the medial and lateral sides of the respective curved bearing surfaces 4a and 4a, the femoral component B is prevented from being inclined or from the thrust in the lateral direction, thereby improving lateral stability. Moreover, a part of the upper face 4 between the pair of bearing surfaces 4a and 4a restricts rotation or recurvatum of the femoral component B.

In order to make better understanding of the above-described functions of the tibial component A with respect to the femoral component B, description will next be made to the femoral component B.

Figure 9:
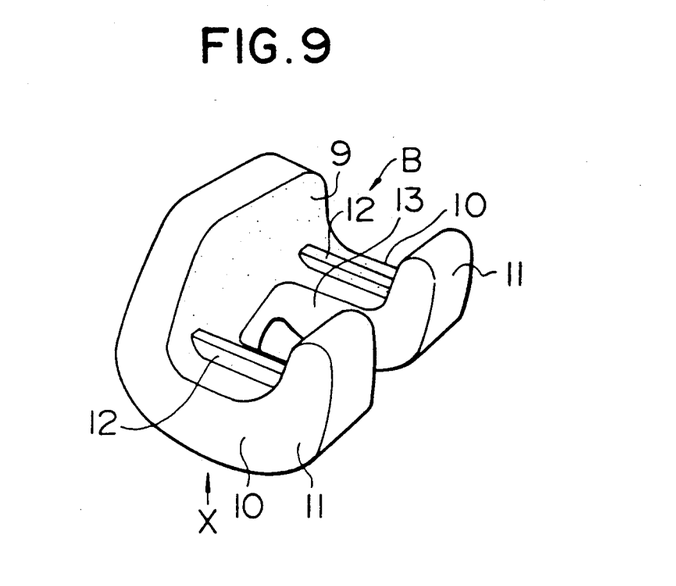
FIG. 9 is a perspective view of the femoral component illustrated in FIG. 8.
Figure 10:
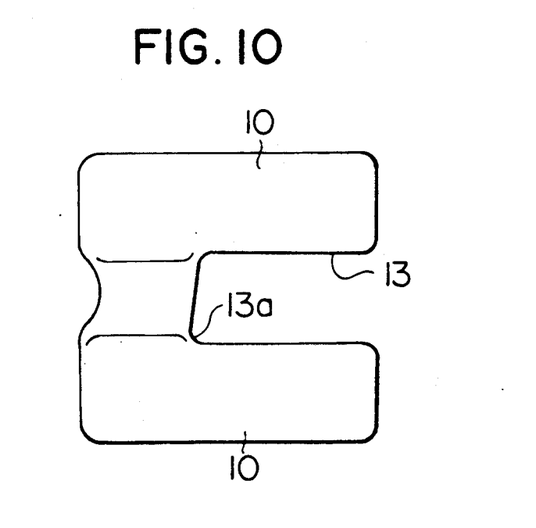
FIG. 10 is a bottom view of the femoral component illustrated in FIG. 9 as viewed from the arrowed direction X.

As shown in FIGS. 9 and 10, the femoral component B comprises an anterior flange 9, a pair of mid sections 10 and 10 receiving the load, a pair of posterior flanges 11 and 11, and a pair of reinforcing beams 12 and 12. A groove 13 is defined between the pair of mid sections 10 and 10. The femoral component B is mounted to the femur D as shown in FIG. 8. The pair of mid sections 10 and 10 have their respective curved lower (articular) faces which are supported by the tibial component A.

The groove 13 has a part 13a which corresponds to the medial condyle of the femoral component B. The cut of the part 13a is made deeply. This is to prevent the component B from compressing the origin of the posterior cruciate ligament at the medial femoral condyle which extends from the medial condyle of the femur D and which attaches to the posterior side of the tibia C. If the groove part 13a is not formed deeply, the origin of the posterior cruciate ligament is compressed and leads to degeneration of the ligament.

Figure 11:
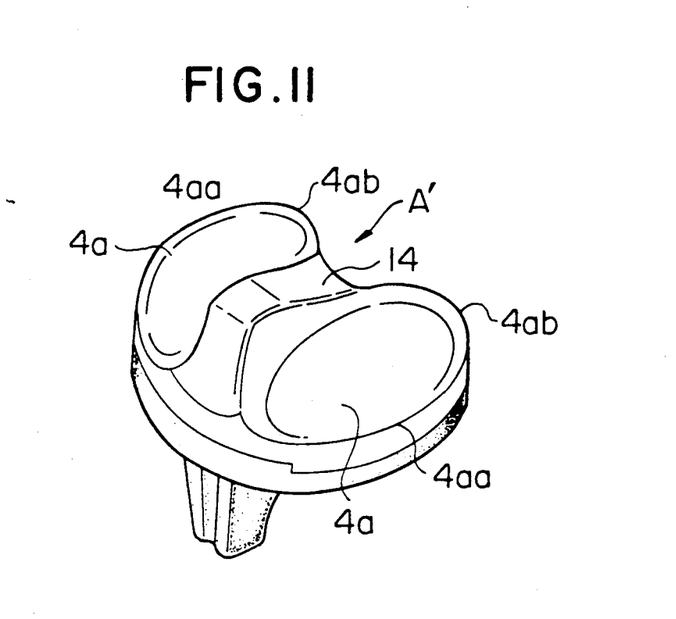
FIG. 11 is a perspective view of a tibial component according to a second embodiment of the invention.
Figure 12:
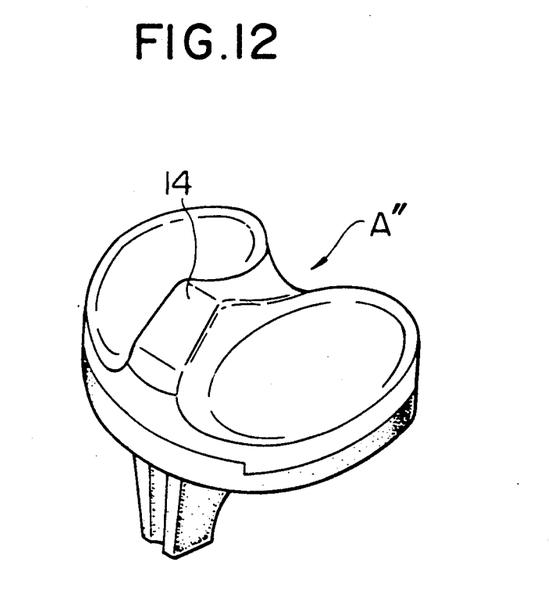
FIG. 12 is a perspective view of a tibial component according to a third embodiment of the invention.

Referring next to FIGS. 11 and 12, there are shown tibial components A' and A" of posterior cruciate ligament sacrificing type, according to a second and a third embodiments of the invention. In FIGS. 11 and 12, parts similar to those illustrated in FIGS. 1 through 10 are designated by the same reference numerals, and the detailed description of such similar parts will therefore be omitted to avoid repetition.

The tibial component A' illustrated in FIG. 11 has a central projection 14 which is provided at a central region of the upper articular surface of the plate section 1. The central projection 14 is high in elevation at the anterior side, and is gradually reduced in height toward the posterior side. Accordingly, the projection 14 restricts sliding movement of the femoral component B in the antero-posterior direction, and also restricts movement of the femoral component B in medio-lateral direction, thereby increasing stability of the femoral component B. Moreover, the pair of bearing surfaces 4a and 4a have their respective outer edges 4aa and 4aa on the medial and lateral direction and respective edges 4ab and 4ab on the posterior side, which are curved upwardly. Further, in the case with the posterior cruciate ligament sacrificed, the tibial component A according to the first embodiment may not be provided with the cut-out 5. However, the cut-out 5 may be provided in order to have a bone projection of the osteotomized end of the tibia to be in mesh with the cut-out 5.

The tibial component A" according to the third embodiment illustrated in FIG. 12 is different in configuration of a central projection 14' from the tibial component A' illustrated in FIG. 11. That is, the central projection 14' becomes high in elevation from the anterior side toward the central part, and again becomes low in elevation toward the posterior side. The central projection 14' has such a function as to restrict rotation of the femoral component B, other than the function of the aforesaid central projection 14.

What is claimed is:

1. A tibial component for use with a femoral component for an artificial knee joint, said tibial component comprising:
   a plate section having, at an upper surface hereof, a pair of bearing surface parts which are adapted to be in sliding contact with said femoral component;
   a stem extending downwardly from a lower surface of said plate section;
   a pair of blade-like plicae extending obliquely posteriorly from said stem and said pair of blade-like plicae extending from said lower surface of said plate section downwardly to an end of said stem remote from said lower surface of said plate section to prevent said stem from being rotated about an axis thereof and for preventing said stem from being inclined in antero-posterior and medio-lateral directions; and
   said plate section having at a lower surface thereof a plurality of elongated grooves for improving affinity with respect to a surrounding bone, said grooves including a first group of grooves and a second group of grooves extending substantially perpendicularly to said first group of grooves.

2. The tibial component according to claim 1, wherein said pair of blade-like plicae defines therebetween an angle of 80° to 140°.

3. The tibial component according to claim 2, wherein said stem is formed at a location adjacent to an anterior part of said plate section from the center thereof, and is inclined posteriorly with respect to a perpendicular to the lower face of said plate section.

4. The tibial component according to claim 2, wherein said stem has a length which is 20% to 75% of a dimension of said plate section in a medio-lateral direction and which is 40% to 90% of a dimension of said plate section in an antero-posterior direction.

5. The tibial component according to claim 2, wherein said stem is rectangular in cross-section.

6. The tibial component according to claim 2, wherein, at a location between said pair of blade-like plicae, said plate section is formed with a curved cut-out into which the posterior cruciate ligament and its surrounding bone are to be inserted.

7. The tibial component according to claim 2, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

8. The tibial component according to claim 2, further comprising a projection formed within a central region of the upper face of said plate section.

9. The tibial component according to claim 1, wherein said stem is formed at a location adjacent to an anterior part of said plate section from the center thereof, and is inclined posteriorly with respect to a perpendicular to the lower face of said plate section.

10. The tibial component according to claim 9, wherein said stem is inclined through 2° to 10° posteriorly with respect to the perpendicular to the lower face of said plate section.

11. The tibial component according to claim 10, wherein said stem has a length which is 20% to 75% of a dimension of said plate section in a medio-lateral direction and which is 40% to 90% of a dimension of said plate section in an antero-posterior direction.

12. The tibial component according to claim 10, wherein said stem is rectangular in cross-section.

13. The tibial component according to claim 10, wherein, at a location between said pair of blade-like plicae, said plate section is formed with a curved cut-out into which the posterior cruciate ligament and its surrounding bone are to be inserted.

14. The tibial component according to claim 10, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

15. The tibial component according to claim 10, further comprising a projection formed within a central region of the upper face of said plate section.

16. The tibial component according to claim 4, wherein said stem has a length which is 20% to 75% of a dimension of said plate section in a medio-lateral direction and which is 40% to 90% of a dimension of said plate section in an antero-posterior direction.

17. The tibial component according to claim 9, wherein said stem is rectangular in cross-section.

18. The tibial component according to claim 9, wherein, at a location between said pair of blade-like plicae, said plate section is formed with a curved cut-out into which the posterior cruciate ligament and its surrounding bone are to be inserted.

19. The tibial component according to claim 9, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

20. The tibial component according to claim 9, further comprising a projection formed within a central region of the upper face of said plate section.

21. The tibial component according to claim 1, wherein said stem has a length which is 20% to 75% of a dimension of said plate section in a medio-lateral direction and which is 40% to 90% of a dimension of said plate section in an antero-posterior direction.

22. The tibial component according to claim 6, wherein said stem is rectangular in cross-section.

23. The tibial component according to claim 21, wherein, at a location between said pair of blade-like plicae, said plate section is formed with a curved cut-out into which the posterior cruciate ligament and its surrounding bone are to be inserted.

24. The tibial component according to claim 21, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

25. The tibial component according to claim 21, further comprising a projection formed within a central region of the upper face of said plate section.

26. The tibial component according to claim 1, wherein said stem is rectangular in cross-section.

27. The tibial component according to claim 26, wherein, at a location between said pair of blade-like plicae, said plate section is formed with a curved cut-out into which the posterior cruciate ligament and its surrounding bone are to be inserted.

28. The tibial component according to claim 26, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

29. The tibial component according to claim 26, further comprising a projection formed within a central region of the upper face of said plate section.

30. The tibial component according to claim 1, wherein, at a location between said pair of blade-like plicae, said plate section is formed with a curved cut-out into which the posterior cruciate ligament and its surrounding bone are to be inserted.

31. The tibial component according to claim 30, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

32. The tibial component according to claim 30, further comprising a projection formed within a central region of the upper face of said plate section.

33. The tibial component according to claim 1, wherein, when said pair of bearing surface parts are considered as a single bearing surface portion, said single bearing surface portion is curved such that an anterior side of said single bearing surface portion is higher in elevation than a posterior side of said single bearing surface portion, and a central side of said single bearing surface portion is higher in elevation than medial and lateral sides of said single bearing surface portion.

34. The tibial component to claim 33, further comprising a projection formed within a central region of the upper face of said plate section.

35. The tibial component according to claim 1, further comprising a projection formed within a central region of the upper face of said plate section.

36. The tibia component according to claim 1, wherein said plate section includes a receiving portion and a pedestal portion which are fixedly connected to each other, said pair of bearing surface parts being formed at an upper surface of said receiving portion, said stem extending downwardly from a lower surface of said pedestal portion, said pedestal portion being made of ceramics.

* * * * *